United States Patent [19]

Dornhofer et al.

[11] Patent Number: 5,753,636
[45] Date of Patent: May 19, 1998

[54] INJECTION SOLUTION FOR INTRAMUSCULAR AND SUBCUTANEOUS ADMINISTRATION TO ANIMALS

[76] Inventors: Winfried Dornhofer, Petzenhofen 17, 82269 Geltendorf, Germany; Erwin Embrechts, Heistraat 2, 2322 Hoogstraten, Belgium

[21] Appl. No.: 553,455
[22] PCT Filed: May 25, 1994
[86] PCT No.: PCT/EP94/01696
    § 371 Date: Feb. 12, 1996
    § 102(e) Date: Feb. 12, 1996
[87] PCT Pub. No.: WO94/27611
    PCT Pub. Date: Dec. 8, 1994

[30] Foreign Application Priority Data

May 26, 1993 [EP] European Pat. Off. ............ 93108460

[51] Int. Cl.⁶ .................... A01N 37/18; A61K 31/65
[52] U.S. Cl. ............................. 514/152; 514/153
[58] Field of Search ............................. 514/153, 152

[56] References Cited

U.S. PATENT DOCUMENTS

| | | | |
|---|---|---|---|
| 2,644,782 | 7/1953 | Harned et al. | 167/65 |
| 2,644,783 | 7/1953 | Weidenheimer et al. | 167/65 |
| 3,557,280 | 1/1971 | Weber et al. | 424/80 |
| 4,018,889 | 4/1977 | Armstrong | 424/80 |
| 4,772,460 | 9/1988 | Malook et al. | 424/10 |

FOREIGN PATENT DOCUMENTS 2047097 11/1980 United Kingdom.

*Primary Examiner*—Marianne M. Cintins
*Assistant Examiner*—Dwayne C. Jones
*Attorney, Agent, or Firm*—Majestic, Parsons, Siebert & Hsue

[57] ABSTRACT

An injection solution for subcutaneous or intramuscular administration to an animal, and a method of producing same, are provided. The injection solution is substantially free of chloride ions and employs a basic amino acid as a pH-adjusting agent, characteristics that make the injection solution more physiologically tolerable upon injection. Preferably, the injection solution comprises 5 to 30 g of oxytetracycline per 100 ml of injection solution, where the oxytetracycline is provided in a magnesium complex; 0 to 25 g of polyvinylpyrrolidone per 100 ml of injection solution; a basic amino acid in an amount sufficient to adjust a pH of the injection solution to from 5.5 to 9.5; and an additive in an aqueous/organic solvent phase.

14 Claims, No Drawings

& # 1

INJECTION SOLUTION FOR INTRAMUSCULAR AND SUBCUTANEOUS ADMINISTRATION TO ANIMALS

This application is a 371 of PCT/EP94/01696 filed May 25, 1994.

FIELD OF THE INVENTION

The invention relates to an injection solution for subcutaneous or intramuscular administration to animals and a process for the production thereof.

BACKGROUND OF THE INVENTION

Tetracycline antibiotics are the agents of first choice in many countries for numerous therapeutic indications in the veterinary sector. Moreover, oxytetracycline (OTC) is the tetracycline used most for parenteral administrations.

Nevertheless, a number of serious problems is associated with the use of tetracyclines. Thus, parenteral use is restricted by their poor solubility and low stability in aqueous media. In addition, they lead to severe irritation at the injection site on intramuscular or subcutaneous injection.

Many attempts have been made to solve the problem of the low solubility of tetracyclines in water by using water-miscible solvents and cosolvents. Examples which may be mentioned are polyethylene glycol, 1,2-propanediol and N,N-dimethylacetalide, which in their turn are highly irritant and have haemolytic effects, NOUWS, Vet. Quart., 1984, 6, 2, 80–84; NOUWS, Vet. Quart., 1990, 12, 3, 129–138; RASMUSSEN et al., Res. vet. Sci., 1976, 20, 55–60; HAPKE et al., DTW, 1983, 90, 161–200 and 216–218.

Better pharmaceutical solutions are obtained by using water-miscible and better tolerated pyrrolidone derivatives which are employed as solubilizers, solvents or cosolvents in aqueous parenteral tetracycline compositions. Reference should be made in this connection to polyvinylpyrrolidone, 2-pyrrolidone, N-methylpyrrolidone and 2-hydroxyethylpyrrolidone. These derivatives permit oxytetracycline formulations of high concentration to be produced.

The advantage of highly concentrated oxytetracycline formulations with 20% OTC is that an antimicrobially effective serum level which persists for up to 72 hours after injection—so-called long-acting formulations (oxytetracycline LA)—can be produced with a single intramuscular injection of a dose of 20 mg per kg of body weight. LA formulations are very popular for administration in veterinary medicine for practical reasons.

Solutions, which are suitable for parenteral, oral and local administration, of oxytetracycline-magnesium complexes in up to 25% strength aqueous polyvinylpyrrolidone with an oxytetracycline content of up to 15% are disclosed in GB-A-1 131 007. The solutions described therein have a pH in the range from 8.0 to 9.5. The pH is adjusted with the aid of sodium hydroxide, ammonia, ethanolamine or ethylenediamine. Solutions of this type are relatively well tolerated but have the disadvantage that the OTC concentration cannot be adjusted to higher than 10% in formulations suitable for parenteral administration. The LA effect of other 20% strength formulations cannot be achieved thereby.

DE-A-26 15 140 discloses an active substance formulation for topical transdermal administration having a vehicle system composed of N-methylpyrrolidone and 2-pyrrolidone in a ratio of 1:4 to 4:1. The vehicle system in the composition described therein is intended to promote passage through the skin of the active substance applied to the skin. Administration of formulations of this type by injection is not intended.

DE-A-26 59 152 describes formulations, which are suitable for injection, of a tetracycline complex in aqueous 2-pyrrolidone, which may additionally contain polyvinylpyrrolidone. However, the solutions described therein have proved to be exceptionally irritant for tissues. The injections are frequently painful for the animals and lead to undesired necroses. The tissue irritation leads to high and long-lasting residue levels in the tissue and result in undesirably long withdrawal periods (Nouws; Rasmussen et al.).

EP-A-0 096 942 describes an oxytetracycline composition in which 10 to 30 parts by weight of oxytetracycline in the form of an alkaline earth metal complex and 2.5 to 10 parts by weight of polyvinylpyrrolidone are dissolved together with antioxidants and bases in aqueous N-methylpyrrolidone at a pH of 6.0 to 9.5. The solutions described therein are intended for intramuscular injection but show the same poor local tolerability as the 2-pyrrolidone formulations described above (Nouws; Rasmussen et al.).

Furthermore, EP-B-0 271 374 describes the use of N-hydroxyethyl-2-pyrrolidone as solubilizer for tetracyclines and, in particular, also for oxytetracycline. No investigations of the tolerability have yet been published.

Another OTC formulation in aqueous/organic solvents has been marketed under the name Tridox. The organic solvent component is a mixture of approximately equal parts of N-methylpyrrolidone and 2-pyrrolidone. The mixture contains polyvinylpyrrolidone to increase the solubility and improve the tolerability. This formulation, which was intended for intramuscular administration, also led to irritation at the injection site. The absorption and the serum levels were not optimal, also because of the irritation.

In all these formulations, the particular tetracycline is first complexed with an alkaline earth metal ion, after which the formulation is adjusted to an advantageous pH. Both serve to improve the chemical and physical stability of the tetracycline solution. It should be noted in this connection that the optimal pH for the various tetracycline derivatives may vary widely and is, for example, for oxytetracycline between 7.5 and 9.5.

Other formulations which correspond in essential points to those indicated above have been disclosed in the past and reflect the many years of research activity in this sector.

The commonest side effect is local irritation at the injection site, which may lead to necroses and encapsulations and reduce or delay the absorption of the active substance. In consequence, long withdrawal periods up to the time of slaughter and, in some cases, a prohibition of use of the tissue lying around the injection site also result.

Veterinary officers and inspectors of slaughter-houses are very familiar with this problem. It is concluded that compositions which lead to severe necroses in muscle tissue no longer meet the current requirements for veterinary medical practice (Vet. Quarterly, 1984, 6, 2, 80–84; ibid., 1990, 12, 3, 129–138). According to these publications, only a single injectable oxytetracycline composition is adjusted to have sufficiently little irritation, namely that described in GB-A-1 131 007. With these compositions, the damage to muscles at the injection site is small and has completely disappeared after a few weeks. However, it has emerged in practice that these solutions can be injected only up to an oxytetracycline content of up to 10%, because of their high viscosity.

The inventors have found that the pharmacokinetic results with the known products also vary widely and substantially correlate with the local irritation in each case. Thus, the serum levels reached on intramuscular administration of these formulations sometimes fall rapidly and sometimes persist for longer but are in each case connected with the more or less severe irritation at the injection sites. The same varying results have also been described in the veterinary medical literature, see MEVIUS et al., Vet. quart., 1986, 8, 4, 285–294; NOUWS, Proc. 2nd Congr. Eur. Assoc. vet. Pharmacol. & Toxicol., Toulouse, France, 1982, 195–198; XIA et al., J. vet. Pharmacol. Ther., 1983, 6, 113–120.

Despite intense research activity, however, it has not to date been possible completely to control the local side effects of LA-OTC product. However, irritation-free long-acting OTC products are very desirable in veterinary practice, not only for reasons of good veterinary practice in respect of the animal to be treated, but also because only they guarantee a safe and reliable shape of the serum curve and allow losses of the injection sites in the carcass to be avoided.

The known LA-oxytetracycline formulations contain the oxytetracycline completed with magnesium, as already mentioned. oxytetracycline hydrochloride and magnesium chloride are often used for the production. The final pH of the formulations is adjusted with organic bases, frequently with mono- or diethanolamiine. In many cases, hydrochloric acid is also added for fine adjustment of the pH. Low polyvinylpyrrolidone concentrations are used to improve the local tolerability, but the amount is limited by the simultaneous increase in the viscosity.

It has now emerged that there is a number of causes of the local irritation at the injection site. The presence of magnesium chloride is an important factor in this connection. Magnesium chloride present in the formulation may, moreover, be attributable to incomplete complexation of magnesium ions or the addition of hydrochloric acid to adjust the pH.

SUMMARY OF THE INVENTION

The object of the invention is to provide OTC injection solutions with reduced tendency to produce local irritation on intramuscular or subcutaneous injection. At the same time, these solutions are intended to ensure serum levels which are at least equivalent to previously known products and to ensure that excretion from the body is as complete as possible.

This object is achieved by an injection solution for subcutaneous or intramuscular administration to animals, according to the present invention. The injection solution has a content, based on 100 ml of solution, of 5 to 30 g of oxytetracycline as magnesium complex, 0 to 25 g of polyvinylpyrrolidone, the required amount of an organic base to adjust a pH of 5.5 to 9.5, and conventional additives in a physiologically tolerated aqueous/organic solvent phase. The injection solution is adjusted to be essentially free of chloride ions and contains a basic amino acid as organic base to adjust the pH.

DESCRIPTION OF EMBODIMENTS

An injection solution for subcutaneous or intramuscular administration to animals, and a process for producing same, are provided according to the present invention. The injection solution comprises, based on 100 ml of solution, 5 to 30 g of oxytetracycline as magnesium complex, 0 to 25 g of polyvinylpyrrolidone, the required amount of an organic base to adjust a pH of 5.5 to 9.5, and conventional additives in a physiologically tolerated aqueous/organic solvent phase.

The use of chloride ions is avoided in the formulation according to the invention, i.e. neither the oxytetracycline nor the magnesium compound used or the complexation is added as chloride. Likewise, hydrochloric acid is not used to correct the pH. The oxytetracycline is expediently added as base, in particular as dihydrate. Magnesium oxide MgO is preferably used as magnesium compound.

To improve the local tolerability of the injection solutions according to the invention further it may be advantageous to employ less than the stoichiometric amount of the magnesium used for complexation of the OTC, for example in a ratio of 0.75:1 to <1:1, preferably in an amount of 0.80:1 to 0.95:1, in each case relative to oxytetracycline. Higher concentrations of free magnesium compounds and, in particular, also MgO are likewise irritant for tissue.

It is known that polyvinylpyrrolidone may improve the local tolerability of tetracyclines. It is therefore worth mentioning that the injection solutions according to the invention show a better local tolerability, even without the addition of polyvinylpyrrolidone, than known products which contain polyvinylpyrrolidone. It might be particularly advantageous to dispense with the addition of polyvinylpyrrolidone because the viscosity of the injection solution increases with such an addition. The injectability of the formulation is made difficult by too high a viscosity.

If polyvinylpyrrolidone is added, it expediently has a molecular weight in the range from 5000 to 30,000. Molecular weights from 10,000 to 17,000 are particularly preferred. Those which are particularly suitable are ones with K values of 12 to 30, for example K12 to K17.

The injection solutions according to the invention contain polyvinylpyrrolidone in an amount of 0 to 0.25 g/100 ml, preferably in an amount of 2.5 to 20 g/100 ml, of solution. A polyvinylpyrrolidone with a low molecular weight is most suitable for the injection solution, for example Kollidon 12 PF from BASF with a K value of 12, in a concentration of about 2.5 to 10 g/100 ml.

It has proved advantageous, in order to increase the tolerability of the injection solutions according to the invention, to dissolve the polyvinylpyrrolidone in water under pressure at a temperature to more than 115° C. This autoclaving process should last at least about 15 min, expediently at least about 30 min. For stabilization and prevention of discoloration it is possible during the autoclaving process to add to the solution sodium metabisulphite, for example in an amount up to 0.5% by weight and preferably of about 0.1% by weight based on the polyvinylpyrrolidone. The autoclaving of the solution additionally improves the injectability even of highly concentrated solutions by about up to 20%.

The oxytetracycline active substance is present in the injection solutions according to the invention in an amount of 5 to 30 g, but in particular in an amount of about 20 g/100 ml of solution.

In the formulations patented to date, organic bases were used to adjust the pH, predominantly mono- or diethanolamine. These products are very irritant, as is evident from studies by T. SADO (Nippon Nogeikagaku Raishi, 1961, 35, 1164–1177). It has been found that basic amino acids such as L-arginine, L-lysine or L-ornithine are suitable replacement products with excellent local tolerability.

The pH in the range from 5.0 to 9.5, preferably 6.0 to 9.5, which is required for the injection solution according to the invention is adjusted according to the invention with a basic amino acid. It is possible to use naturally occurring or synthetic amino acids, with the L form, which is more physiologically tolerable, being preferred in each case. A basic amino acid means according to the invention one which contains at least 2 amino groups together with at least one acidic group, with the number of amino groups exceeding that of the acidic groups. An acidic group means, as a rule, a carboxylic acid group, but other acidic groups may also fulfill the desired purpose, for example a sulphonic acid group.

The use of the natural basic amino acids L-arginine, L-lysine and L-ornithine is particularly preferred. The potential irritation associated with the use of sodium hydroxide or organic amines is avoided in this way.

It has emerged that the use of basic amino acids distinctly improves the tolerability of the formulations produced therewith. However, it may be expedient to add additional conventional bases in small amounts in order to facilitate the pH adjustment or to prevent the precipitation of the amino acid because the solubility has been exceeded.

The good tolerability of the injection solutions according to the invention is furthermore determined by the use of starting materials free of chloride ions. The terms "free of chloride ions" or "essentially free of chloride ions" used here mean that the content of chloride ions is of an order of magnitude at which physiological irritation can no longer be caused.

In principle, the solutions according to the invention can be produced from any desired starting materials, even those containing chloride. It is then necessary, for adjustment to freedom from chloride ions, to take measures for removing disadvantageous amounts of chloride from the finished solution. This can take place, for example, by in fact preparing the magnesium complexes starting from starting materials which contain chloride ions, such as hydrochlorides and magnesium chloride, but removing the chlorides produced thereby, for example by crystallization. In order to obtain a product which is essentially free of chloride ions, however, it is always preferable to use a magnesium salt which is free of chloride ions, in particular magnesium oxide. Oxytetracycline is preferably employed in the form of the free base, in particular as dehydrate. It is furthermore possible to use salts which are free of chloride ions and whose tolerability and low irritation is known.

The injection solutions according to the invention are preferably adjusted to an injection viscosity of less than 70 cps. An injection viscosity of less than 40 cps is particularly preferred.

Conventional organic solvents can be employed for the aqueous/organic solvent phase for oxytetracycline formulations. Their physiological tolerability is a precondition. Pyrrolidone and its derivatives, in particular N-methylpyrrolidone, 2-pyrrolidone and N-(2-hydroxyethyl)pyrrolidone have proved suitable. Mention should also be made of N,N-dimethylacetamide, hydroxyethylacetamide and other conventional amide derivatives, glycerol formal, polyethylene glycol and polypropylene glycol. Preferred aqueous/organic solvents are N-methylpyrrolidone and 2-pyrrolidone.

The injection solutions according to the invention can be produced both with the individual solvents and with mixtures thereof. It has been found that, in particular, mixtures of two different solvents of the pyrrolidone type further improve the absorption characteristics compared with the use of the particular solvent alone. References to this effect are to be found in DE-A-2 615 140, but for the case of transdermal formulations therein. However, the same effect also occurs on subcutaneous or intramuscular administration.

The injection solutions according to the invention expediently contain 8 to 66 g of solvent per 100 ml of solution.

Formulations with an oxytetracycline content of about 10 to 30 g, in particular about 20 g, per 100 ml of solution have proved particularly suitable for intramuscular administration. A preferred formulation contains in the solvent phase 20 to 60 g of N-methylpyrrolidone and 2-pyrrolidone in a mixing ratio of 92:8 to 70:30. To stabilize the solution and increase the tolerability it is possible to add 2.5 to 10 g of polyvinylpyrrolidone per 100 ml of solution.

In this case the weight ratio of N-methyl-pyrrolidone to 2-pyrrolidone is preferably less than 90:10 and larger than 80:20 and is, in particular, about 5:1 to 4:1. It has emerged that, when these limits are observed, an optimum dissolving effect with good injectability and good tolerability is achieved. At the same time, the mixture guarantees good absorption of the pharmaceutical after intramuscular or subcutaneous injection, so that the desired high serum levels are reached at an early time. Tissue residues are completely broken down within a short time so that the result is a shortening of the withdrawal periods which have had to be observed to date.

The excellent pharmacokinetic properties of the injection solutions according to the invention have been confirmed by examination of classical serum curves. The serum creatine phosphokinase levels (CK) showed an excellent local tolerability which was superior to previously disclosed products and was confirmed by the known Shintani test.

The pharmacokinetic properties of the solutions according to the invention have been investigated by determining the classical serum curves in calves. Determination of serum oxytetracycline in this case took place by means of high pressure liquid chromatography.

It is known that damage to the skeletal muscle causes an increase in serun CK activity. The increase in the CK activity depends on the extent of the traumatization, for example also of the intramuscular injection of certain pharmaceuticals (veterinärmedizinische Laboruntersuchungen für die Diagnose und Verlaufskontrolle [veterinary medical laboratory tests for diagnosis and monitoring progress], Boehringer Mannheim; UCELLI et al., Rec. med. vet., 1988, 164, 11, 939–943).

The increase in the CK levels was investigated in calves after a single intramuscular administration of various products. 4 calves in each trial group were selected at random, with the sex (female), breed (black and white) and body weight (110±2 kg) being consistent. The animals received a single intramuscular treatment, the therapeutic dose being one ml of product per 10 kg of body weight (20 mg of oxytetracycline per kg of body weight). Blood samples were taken immediately before and 8, 12, 24, 48, 60, 72 and 96 hours after the injection. The CK determinations took place by automatic analysis as described by Boehringer Mannheim with a BM/Hitachi 704 apparatus. The formulation of Example 7 according to the invention was compared with a commercially available product (20% of oxytetracycline in aqueous 2-pyrrolidone).

|  | Hours after injection | | | | | | |
| --- | --- | --- | --- | --- | --- | --- | --- |
| CK levels in IU/l (means) | 0 | 8 | 12 | 24 | 48 | 72 | 96 |
| Formula Example 7 | 18 | 79 | 55 | 34 | 23 | 22 | 20 |
| Non-commercial | 22 | 291 | 163 | 98 | 58 | 49 | 26 |

| | Hours after injection |
|---|---|
| Oxytetracycline 20% in 2-pyrr. | |

It is evident from the results that the injection solution according to Example 7 resulted in only an approximately 4-fold increase in the CK levels, which had essentially disappeared completely after 48 hours. By contrast, an approximately 13-fold increase in the CK levels occurred in the comparison product and did not disappear again until 92 hours had elapsed.

A check by the Shintani test (Shintani et al., Tox. appl. Pharmacol., 1967, 11, 293–301) confirmed the results of the CK test. The degree of irritation was determined on the basis of a macroscopic assessment of the injection site after intramuscular administration to rabbits.

| SHINTANI SCORE | Hours after injection | |
|---|---|---|
| (Mean of 3 animals in each case) | 48 | 72 |
| Formula Example 3 | 3.00 (*) | 2.00 |
| Commercial oxytetracycline 20% N-methylpyrrolidone | 4.33 | 3.33 |

The Shintani criteria are:

| no reaction: | 0 to 0.4 |
|---|---|
| slight reaction: | 0.5 to 1.4 |
| mild reaction: | 1.5 to 2.4 |
| moderate reaction: | 2.5 to 3.4 |
| strong reaction: | 3.5 to 4.4 |
| serious reaction: | 4.5 to 5 |

(*) 3.00 only because of yellow precipitation. The injection site was, however, free of necroses.

The formulations according to the invention are preferably produced by a process in which, in a first step, the required amount of polyvinylpyrrolidone is dissolved in water and autoclaved at a temperature of more than 115° C. for a period of at least 15 min, in a second step this solution is, after cooling, mixed with one or more organic solvents which are physiologically advantageous, stabilizers and a chloride-free magnesium salt in each case in the required amounts, and stirred to homogeneity, and thien, in a third step, the required amount of oxytetracycline or oxytetracycline derivative, which is free of chloride ions, is stirred in, with the required pH being adjusted by adding the basic amino acid. In the case where no polyvinylpyrrolidone is present in the formulation according to the invention, of course, the autoclaving step is dispensed with.

The invention is explained in detail by the following examples.

Production process

The following Examples 1 to 8 were carried out with the following production process.

Where present, the polyvinylpyrrolidone was mixed together with the sodium metabisulphite in about 25 ml of water for injection and autoclaved at 121° C. for 30 min. After cooling to room temperature, the organic solvent phase (2-pyrrolidone and/or N-methylpyrrolidone) was mixed in, followed by the magnesium oxide. Mixing was continued until a homogeneous suspension was obtained.

The resulting mixture was subsequently mixed with sodium formaldehyde sulphoxylate and the basic imino acid. The mixture was heated to 50° C. and oxytetracycline dihydrate was slowly added, while continuing the stirring. Heating was continued until the oxytetracycline was completely complexed.

After cooling to room temperature, the mixture was diluted to 100 ml with water for injections. The solution was sterile filtered and dispensed into ampoules under nitrogen as protective gas.

Example 1

| | |
|---|---|
| Oxytetracycline dihydrate (equivalent to 20 g of oxytetracycline) | 21.600 g |
| Magnesium oxide | 1.600 g |
| Polyvinylpyrrolidone (K17) | 5.000 g |
| Sodium metabisulphite | 0.005 g |
| 2-Pyrrolidone | 8.880 g |
| N-Methylpyrrolidone | 41.200 g |
| Sodium formaldehyde sulphoxylate | 0.400 g |
| L-Arginine | 3.250 g |
| Water for injections | to 100 ml |

The pH of the solution was 8.90.

Example 2

| | |
|---|---|
| Oxytetracycline dihydrate (equivalent to 20 g of oxytetracycline) | 21.600 g |
| Magnesium oxide | 1.600 g |
| Polyvinylpyrrolidone (K17) | 5.000 g |
| Sodium metabisulphite | 0.005 g |
| 2-Pyrrolidone | 50.000 g |
| Sodium formaldehyde sulphoxylate | 0.400 g |
| L-Arginine | 3.650 g |
| Water for injections | to 100 ml |

The pH of the solution was 8.74.

Example 3

| | |
|---|---|
| Oxytetracycline dihydrate (equivalent to 20 g of oxytetracycline) | 21.600 g |
| Magnesium oxide | 1.600 g |
| Polyvinylpyrrolidone (K17) | 8.000 g |
| Sodium metabisulphite | 0.008 g |
| 2-Pyrrolidone | 8.880 g |
| N-Methylpyrrolidone | 41.200 g |
| Sodium formaldehyde sulphoxylate | 0.400 g |
| L-Arginine | 3.250 g |
| Water for injections | to 100 ml |

The pH of the solution was 8.90.
The viscosity at 25° C. was 45 cst.

Example 4

| | |
|---|---|
| Oxytetracycline dihydrate (equivalent to 20 g of oxytetracycline) | 21.600 g |
| Magnesium oxide | 1.450 g |
| 2-Pyrrolidone | 8.880 g |
| N-Methylpyrrolidone | 41.200 g |
| Sodium formaldehyde sulphoxylate | 0.400 g |
| L-Arginine | 3.750 g |
| Water for injections | to 100 ml |

The pH of the solution was 8.73.

Example 5

| | |
|---|---|
| Oxytetracycline dihydrate (equivalent to 20 g of oxytetracycline) | 21.600 g |
| Magnesium oxide | 1.600 g |
| Polyvinylpyrrolidone (K17) | 8.000 g |
| Sodium metabisulphite | 0.008 g |
| 2-Pyrrolidone | 8.880 g |
| N-Methylpyrrolidone | 41.200 g |
| Sodium formaldehyde sulphoxylate | 0.400 g |
| L-Cystein | 0.025 g |
| L-Arginine | 3.250 g |
| Water for injections | to 100 ml |

The pH of the solution was 8.77.
The viscosity at 25° C. was 44 cst.

Example 6

| | |
|---|---|
| Oxytetracycline dihydrate (equivalent to 20 g of oxytetracycline) | 21.600 g |
| Magnesium oxide | 1.450 g |
| Polyvinylpyrrolidone (K12) | 8.000 g |

-continued

| | |
|---|---|
| Sodium metabisulphite | 0.008 g |
| 2-Pyrrolidone | 8.880 g |
| N-Methylpyrrolidone | 41.200 g |
| Sodium formaldehyde sulphoxylate | 0.400 g |
| L-Arginine | 3.750 g |
| Water for injections | to 100 ml |

The pH of the solution was 8.77.

Example 7

| | |
|---|---|
| Oxytetracycline dihydrate (equivalent to 20 g of oxytetracycline) | 21.600 g |
| Magnesium oxide | 1.450 g |
| Polyvinylpyrrolidone (K17) | 2.500 g |
| Sodium metabisulphite | 0.002 g |
| 2-Pyrrolidone | 8.880 g |
| N-Methylpyrrolidone | 41.200 g |
| Sodium formaldehyde sulphoxylate | 0.400 g |
| L-Arginine | 3.750 g |
| Water for injections | to 100 ml |

The pH of the solution was 8.83.

Example 8

| | |
|---|---|
| Oxytetracycline dihydrate (equivalent to 30 g of oxytetracycline) | 33.570 g |
| Magnesium oxide | 2.300 g |
| Polyvinylpyrrolidone (K17) | 8.000 g |
| Sodium metabisulphite | 0.008 g |
| 2-Pyrrolidone | 9.000 g |
| N-Methylpyrrolidone | 49.000 g |
| Sodium formaldehyde sulphoxylate | 0.400 g |
| L-Arginine | 6.500 g |
| Water for injections | to 100 ml |

The pH of the solution was 8.60.

We claim:

1. An injection solution for intramuscular or subcutaneous administration to an animal, comprising:

5 to 30 g of oxytetracycline per 100 ml of injection solution, the oxytetracycline in a magnesium complex;

0 to 25 g of polyvinylpyrrolidone per 100 ml of injection solution;

a basic amino acid in an amount sufficient to adjust a pH of the injection solution to a range of 5.5 to 9.5; and an additive in an aqueous/organic solvent phase;

the injection solution being substantially free of chloride ions.

2. The injection solution according to claim 1, comprising 2.5 to 20 g of polyvinylpyrrolidone per 100 ml of solution, the polyvinylpyrrolidone having a molecular weight of 500 to 30,000.

3. The injection solution according to claim 2, wherein the polyvinylpyrrolidone has a K value of 12 to 30.

4. The injection solution according to claim 2 wherein the polyvinylpyrrolidone is obtained by autoclaving an aqueous solution of polyvinylpyrrolidone at above 115° C. for at least 15 min.

5. The injection solution according to claim 4, wherein the polyvinylpyrrolidone is obtained by autoclaving the aqueous solution in the presence of sodium metabisulphite in an amount of up to 0.5% by weight based on the polyvinylpyrrolidone.

6. The injection solution according to any of claims 1 to 5, wherein the basic amino acid comprises L-arginine, L-lysine, L-ornithine or a mixture thereof.

7. The injection solution according to any of claims 1 to 5 having an injection viscosity of less than 70 cps.

8. The injection solution according to any of claims 1 to 5, comprising 20 g of oxytetracycline per 100 ml of injection solution.

9. The injection solution according to any of claims 1 to 5, wherein the additive comprises 2-pyrrolidone, N-methylpyrrolidone, N-hydroxyethylpyrrolidone or a mixture thereof in an organic solvent phase.

10. The injection solution according to claim 9, wherein the additive comprises 8 to 66 g of N-hydroxyethylpyrrolidone and 2-pyrrolidone per 100 ml of injection solution in a weight ratio of 92:8 to 70:30.

11. The injection solution according to any of claims 1 to 5, wherein the magnesium complex has a molar ratio of magnesium to oxytetracycline of 0.80:1 to 0.95:1.

12. A method of producing an injection solution for intramuscular or subcutaneous administration to an animal, comprising:

providing an aqueous solution of polyvinylpyrrolidone and autoclaving the aqueous solution at more than 115° C. for at least 15 min;

cooling the aqueous solution and mixing the aqueous solution with at least one physiologically tolerable, water-miscible organic solvent, at least one stabilizer and a magnesium compound which is substantially free of chloride ions to form a homogeneous solution;

mixing the homogeneous solution with oxytetracycline or an oxytetracycline derivative which is substantially free of chloride ions; and adding a basic amino acid to adjust pH.

13. The method according to claim 12, wherein the oxytetracycline is a base, the magnesium compound is magnesium oxide and the basic amino acid is L-arginine.

14. The method according to claim 13, wherein the magnesium oxide is provided in less than a stoichiometric amount.

* * * * *